United States Patent [19]

Woschina et al.

[11] Patent Number: 4,960,937
[45] Date of Patent: Oct. 2, 1990

[54] PROCESS FOR THE PREPARATION OF TRANS-1,1,2-TRIPHENYL-BUT-1-ENE DERIVATIVES

[75] Inventors: Axel Woschina, Poing; Helmut Grill, Vaterstetten, both of Fed. Rep. of Germany

[73] Assignee: Klinge Pharma GmbH, Munich, Fed. Rep. of Germany

[21] Appl. No.: 263,209

[22] Filed: Oct. 27, 1988

[30] Foreign Application Priority Data

Oct. 29, 1987 [DE] Fed. Rep. of Germany ....... 3736682

[51] Int. Cl.$^5$ ........................................... C07C 213/08
[52] U.S. Cl. ..................................................... 564/324
[58] Field of Search ......................................... 564/324

[56] References Cited

U.S. PATENT DOCUMENTS 4,536,516  8/1985  Harper et al. ..................... 514/514

FOREIGN PATENT DOCUMENTS 0127128  12/1984  European Pat. Off. .
1013907  12/1965  United Kingdom .

OTHER PUBLICATIONS

Robertson et al. "Synthesis of E and Z Isomers of the Antiestrogen Tamoxifen, etc.", J. Org. Chem 47 2387–2393 (1982).

Journal of Chromatography, "Separation of Tamoxifen Geometric Isomers & Metabolites by Bonded-Phase B–Cyclodextrin Chromatography", Armstrong et al., vol. 414 (1987), pp. 192–196.

Acta Chimica Academine Scientiarum Hungavicae, "Synthesis and Structure Determination of Geometric Isomers of 1-Aryl-2-Ethyl-1,2-Diphenylethylenes by $^1$H-NMR Spectroscopy", pp. 69–74 (1979).

Primary Examiner—Glennon H. Hollrah
Assistant Examiner—P. O'Sullivan
Attorney, Agent, or Firm—Sughrue, Mion, Zinn, Macpeak & Seas

[57] ABSTRACT

The invention concerns the direct preparation of trans-1,1,2-triphenyl-but-1-ene derivatives having the general formula 1 by dehydration of carbinols having the general formula 2 by heating in a strongly hydrochloric or sulphuric acid medium with the exclusion of organic solvents.

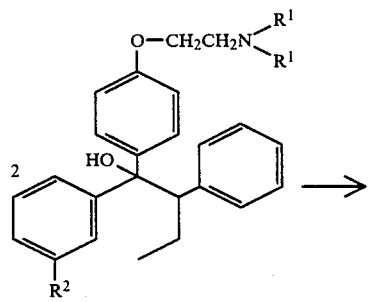

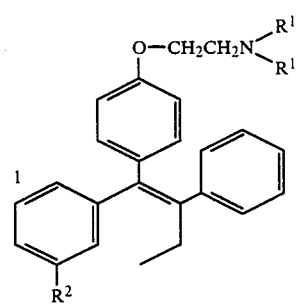

$R^1$ = —CH$_3$, —CH$_2$CH$_3$; $R^2$ = —H, —OH.

7 Claims, No Drawings

PROCESS FOR THE PREPARATION OF TRANS-1,1,2-TRIPHENYL-BUT-1-ENE DERIVATIVES

In recent years a series of triphenylbutene derivatives has been described which are suitable because of their antioestrogic properties for the treatment of hormone-dependent mamma tumors (R. Sutherland and V.C. Jordan, "Nonsteroidal Antioestrogens" Academic Press, 1981).

The active ingredient 1-[4'-(2-dimethylaminoethoxy)phenyl]-trans-1,2-diphenyl-but-1-ene has entered into the therapy, and in the meantime has become known throughout the world by the designation TAMOXIFEN (INN).

When synthesising 1,1,2-triphenyl-but-1-ene derivatives, there accumulate in the dehydration stage of the diastereomeric carbinols of formula 2 the geometrically isomeric olefins of formulae 3 and 1 [cis/trans- or E/Z-form] in the mixture.

Chem. 25, 1056–1060 (1982); R. D. Armstrong, J. Chromatogr. 414, 192–196 (1987)].

The unsatisfactory yield of Tamoxifen could only be increased when it became possible to subject the previously worthless mother liquor fractions which are enriched with the cis-form to a conversion into the trans-form. As can be seen from European Pat. No. 0 127 128, the cis-form can be converted into the trans-form in a strongly hydrochloric acid milieu at increased temperature.

Surprisingly a substantial simplification in the process for the preparation of trans-1,1,2-triphenyl-but-1-ene derivatives of the general formula 1 has now become possible. As will be shown, carbinol compounds having the general formula 2 can under certain conditions be largely transformed in a single step into the trans-olefins having the general formula 1. Thereby the stages which were necessary in the previous preparation processes:

a) isolation of the cis/trans isomer mixture after dehydration of the diastereomeric carbinols, b) separation of the trans-form by crystallization or

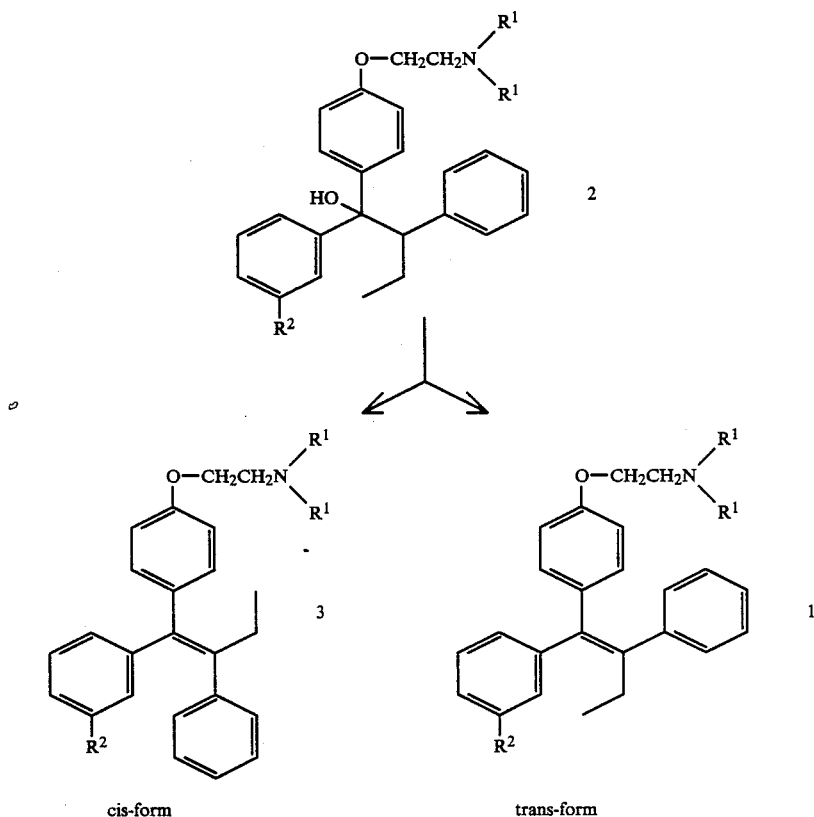

$R^1 = -CH_3, -CH_2CH_3; R^2 = -H, OH.$

Because only the active isomer can be considered for clinical application, it was necessary to isolate the pure trans-form from the resulting isomer mixture. This was done until now by costly processes making heavy losses such as fractionated crystallization or by chromatography. [UK Pat. No. 1 013 907; U.S. Pat. No. 4,536,516; European Pat. No. 0 054 168; G. R. Bedford and D. N. Richardson, Nature 212, 733–734 (1966); P. Sohar et al., Acta Chim. Acad. Sci. Hung. 100, 69–74 (1979); D. W. Robertson and J. A. Katzenellenbogen J. Org. Chem. 47, 2387–2393 (1982); P. C. Ruenitz et al., J. Med.

by chromatography and c) re-isomerization of the mother liquor fractions enriched with the cis-form can be omitted totally.

In the process according to the invention carbinols of the general formula 2 are transformed directly into the trans-olefins of formula 1 in the absence of organic solvents by the influence of hydrochloric acid or of sulphuric acid at increased temperature. Under these conditions, the formation of cis-olefins of formula 3 is practically suppressed.

The conversion of the carbinols in accordance with formula 2 into the trans-olefins of formula 1 is carried out for preference in the temperature range from 50° to 60° C. Hydrochloric or sulphuric acid is permitted to take effect at increased temperature, preferably for from 12 to 16 hours, but at least for 10 hours.

The invention will be explained in more detail on the basis of the examples of embodiments given below.

EXAMPLE 1

1 part of 1-[4'-(2-dimethylaminoethoxy)phenyl]-1,2-diphenyl-butane-1-ol is stirred in ten parts of 50 % by volume sulphuric acid, and the suspension is heated for 14 hours with intensive stirring to 55° C. Subsequently cooling is carried out and with the addition of 2.5 parts ice and 12.5 parts of concentrated ammonia, alkalization is performed. The reaction product is taken up in ethylacetate and the organic phase is washed repeatedly with water. After the removal of the organic solvent in the vacuum 0.9 parts of residue remain with a content of 1-[4'-(2-dimethylaminoethoxy)phenyl]-trans-1,2-diphenyl-but-1-ene of 94 % [HPLC]. Crystals from acetone have a melting point of 98° C. Content: 99.4 % [HPLC].

EXAMPLE 2

1 part of 1-[4'-(2-dimethylaminoethoxy)phenyl]-1,2-diphenyl-butane-1-ol is stirred in 6 parts of 32 % by weight hydrochloric acid and the suspension is heated for 16 hours with intensive stirring to 52° C. Subsequently cooling is performed and with the addition of 2 parts of ice and 6 parts of concentrated ammonia, alkalization is carried out. The reaction product is taken up in ethylacetate and the organic phase is washed repeatedly with water. After the removal of the organic solvent in the vacuum, 0.97 parts of residue remain with a content of 1-[4'-(2-dimethylaminoethoxy)phenyl]-trans-1,2-diphenyl- but-1-ene of 96 % [HPLC]. Crystals from methanol/water have a melting point of 96 to 98° C; content: 99.7 % [HPLC]

EXAMPLE 3

1 part of 1-[4'-(2-dimethylaminoethoxy)phenyl]-1(3'-hydroxyphenyl) - 2-phenyl-butane-1-ol is stirred in 9 parts of 50.% by volume sulphuric acid and the suspension is heated for 15 hours with intensive stirring to 52° C. Subsequently cooling is carried out and alkalization is performed with the addition of 3 parts of ice and 12 parts concentrated ammonia. The reaction product is taken up in dichloromethane and the organic phase is repeatedly washed with water. After the removal of the organic solvent in the vacuum 0.9 parts of residue remain with a content of 1-[4'-(2-dimethylaminoethoxy)-phenyl]-trans-1-(3'-hydroxyphenyl)-2-phenyl-but-1-ene of 90 % [HPLC]. Crystals from ethanol have a melting point of 164° C; content: 99.5 % [HPLC].

EXAMPLE 4

1 part 1-[4'-(2-dimethylaminoethoxy)phenyl]-1-(3'-hydroxy- phenyl)-2-phenyl-butane-1-ol is stirred in 6 parts of 37 % by weight hydrochloric acid and the suspension is heated for 16 hours to 50° C with intensive stirring. Subsequently cooling is effected and alkalization is carried out with the addition of 3 parts of ice and 4 parts concentrated ammonia. The reaction product is taken up in dichloromethane and the organic phase is repeatedly washed with water. After the removal of the organic solvent in the vacuum 0.85 parts of residue remain with a content of 1-[4'-(2-dimethylaminoethoxy)-phenyl]-trans-1-(3'-hydroxy- phenyl)-2-phenyl-but-1-ene of 93 % [HPLC]. Crystals from ethanol have a melting point of 164° C; content: 99.6 % [HPLC].

EXAMPLE 5

1 part of 1-[4'-(2-diethylaminoethoxy)phenyl]-1-(3-hydroxyphenyl)-2-phenyl-butane-1-ol is stirred in 8 parts of 37 % by weight hydrochloric acid and the suspension is heated for 15 hours to 52° C with intensive stirring. Subsequently cooling is carried out and alkalization is performed with the addition of 4 parts of ice and 5 parts concentrated ammonia. The reaction product is taken up in dichloromethane and the organic phase is washed repeatedly with water. After the removal of the organic solvent in the vacuum 0.95 parts of residue remain with a content of 1-[4'-(2-diethylaminoethoxy)-phenyl]-trans-1-(3'-hydroxy- phenyl)-2-phenyl-but-1-ene of 95 % [HPLC]. Crystals from isopropanol have a melting point of130° C; content: 99.5 % [HPLC].

We claim:

1. A process for the preparation of trans-1,1,2-triphenyl-but-1-ene derivatives having the general formula 1

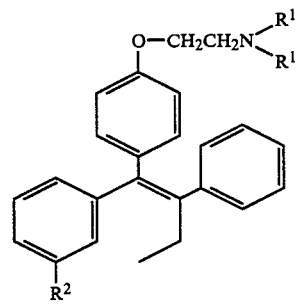

in which $R^1$=CH$_3$, CH$_2$CH$_3$ and $R^2$=H, OH, wherein carbinols having the general formula 2

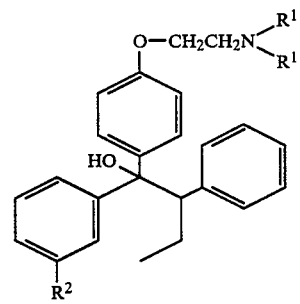

in which $R^1$ and $R_2$ possess the meaning which is given in formula 1 are heated for 10–16 hours at a temperature of from 50°–60° C. in a strongly hydrochloric of sulphuric acid medium with the exclusion or organic solvents and wherein the reaction product is recovered by conventional methods.

2. A process as set forth in claim 1, wherein the hydrochloric acid concentration amounts to at least 25% by weight or wherein the sulphuric acid concentration is at least 40% by volume.

3. A process as set forth in claim 2, wherein said heating is carried out at a temperature of from 50°–55° C.

4. A process as set forth in claim 1, wherein said heating is carried out at a temperature of from 50°–55° C.

5. A process as set forth in claim 1, wherein the hydrochloric acid concentration is from 32–37% by weight.

6. A process as set forth in claim 1, wherein the sulphuric acid concentration is from 45–50% by volume.

7. A process as set forth in claim 1, wherein said heating is carried out from 12–16 hours at a temperature of from 50°–55° C.

* * * * *